United States Patent
Drake, Jr.

(10) Patent No.: US 6,657,733 B1
(45) Date of Patent: *Dec. 2, 2003

(54) METHOD AND APPARATUS FOR DETECTING ULTRASONIC SURFACE DISPLACEMENTS USING POST-COLLECTION OPTICAL AMPLIFICATION

(75) Inventor: Thomas E. Drake, Jr., Fort Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/416,399

(22) Filed: Oct. 12, 1999

Related U.S. Application Data

(63) Continuation-in-part of application No. 09/345,558, filed on Jun. 30, 1999, now Pat. No. 6,122,060.
(60) Provisional application No. 60/091,229, filed on Jun. 30, 1998.

(51) Int. Cl.⁷ .............................................. G01B 11/02
(52) U.S. Cl. ........................................ 356/511; 356/432
(58) Field of Search ................................ 356/502, 511, 356/498, 493, 486

(56) References Cited

U.S. PATENT DOCUMENTS

| | | | |
|---|---|---|---|
| 4,659,224 A | * | 4/1987 | Monchalin .................. 356/352 |
| 5,080,491 A | | 1/1992 | Monchalin et al. .......... 356/352 |
| 5,131,748 A | | 7/1992 | Monchalin et al. .......... 356/349 |
| 5,339,289 A | | 8/1994 | Erickson ...................... 367/149 |
| 5,604,592 A | | 2/1997 | Kotidis et al. ............... 356/357 |
| 5,608,166 A | | 3/1997 | Monchalin et al. ........... 73/657 |
| 5,672,830 A | | 9/1997 | Rogers et al. ................ 73/597 |
| 6,122,060 A | * | 9/2000 | Drake, Jr. .................... 356/359 |
| 6,182,512 B1 | * | 2/2001 | Lorraine ...................... 73/655 |

FOREIGN PATENT DOCUMENTS

EP    0 432 963 A2    5/1990

OTHER PUBLICATIONS

International Search Report issued to corresponding PCT Application No. PCT/US00/41128 dated Apr. 4, 2001.

* cited by examiner

Primary Examiner—Frank G. Font
Assistant Examiner—Phil Natividad
(74) Attorney, Agent, or Firm—Koestner Bertani LLP

(57) ABSTRACT

The present invention detects ultrasonic displacements includes a detection laser to generate a first pulsed laser beam to detect the ultrasonic surface displacements on a surface of the target. Collection optics to collect phase modulated light from the first pulsed laser beam either reflected or scattered by the target. An optical amplifier which amplifies the phase modulated light collected by the collection optics. An interferometer which processes the phase modulated light and generate at least one output signal. A processor that processes the at least one output signal to obtain data representative of the ultrasonic surface displacement at the target.

8 Claims, 4 Drawing Sheets

CH1 P-P=12.8mV

CH1 P-P=108mV

METHOD AND APPARATUS FOR DETECTING ULTRASONIC SURFACE DISPLACEMENTS USING POST-COLLECTION OPTICAL AMPLIFICATION

RELATED APPLICATIONS

This application claims the benefit of U.S. Provisional Application No. 60/091,229 filed on Jun. 30, 1998. Additionally this application claims priority to and repeats a substantial portion of prior application entitled METHOD AND APPARATUS FOR DETECTING ULTRASONIC SURFACE DISPLACEMENTS USING POST-COLLECTION OPTICAL AMPLIFICATION filed on Jun. 30, 1999, which was accorded Ser. No. 09/345,558, now U.S. Pat. No. 6,122,060, since this application names the inventor named in the prior application, the application constitutes a continuation-in-part of the prior application. This application incorporates by reference the prior U.S. Provisional Application No. 60/091,240 filed on Jun. 30, 1998 entitled "METHOD AND APPARATUS FOR ULTRASONIC LASER TESTING" to Thomas E. Drake and U.S. patent application Ser. No. 09/345,558 filed on Jun. 30, 1999 entitled "METHOD AND APPARATUS FOR DETECTING ULTRASONIC SURFACE DISPLACEMENTS USING POST-COLLECTION OPTICAL AMPLIFICATION" to Thomas E. Drake.

TECHNICAL FIELD OF THE INVENTION

The present invention relates generally to a system and method of non-destructive evaluation of materials, and more particularly, to a system and method of processing optical information to detect ultrasonic surface displacements through the use of at least one laser and optically amplifying the scattered return of laser light after collecting it to perform a non-destructive evaluation of a material.

BACKGROUND OF THE INVENTION

In recent years, the use of advanced composite structures has experienced tremendous growth in the aerospace, automotive, and many other commercial industries. While composite materials offer significant improvements in performance, they require strict quality control procedures in the manufacturing processes. Specifically, non-destructive evaluation ("NDE") methods are required to assess the structural integrity of composite structures, for example, to detect inclusions, delaminations and porosities. Conventional NDE methods, however, are very slow, labor-intensive, and costly. As a result, testing procedures adversely increase the manufacturing costs associated with composite structures.

Various systems and techniques have been proposed to assess the structural integrity of composite structures. One method to generate and detect ultrasound using lasers is disclosed in U.S. Pat. No. 5,608,166, issued Mar. 4, 1997, to Monchalin et al. (the "166 patent"). The '166 patent discloses the use of a first modulated, pulsed laser beam for generating ultrasound on a work piece and second pulsed laser beam for detecting the ultrasound. Phase modulated light from the second laser beam is then demodulated to obtain a signal representative of the ultrasonic motion at the surface of the work piece. A disadvantage of such a system has been that in order to improve the systems ability to detect ultrasonic motion at the surface of the work piece a more powerful laser is required which may be impractical to construct or could damage the work piece due to excessive heating.

Another method to generate and detect ultrasound using lasers is disclosed in U.S. patent application Ser. No. 60/091,240 filed on Jun. 30, 1998 to T. E. Drake entitled "Method And Apparatus for Ultrasonic Laser Testing" hereafter DRAKE. DRAKE discloses the use of a first modulated, pulsed laser beam for generating ultrasound on a work piece and a second pulsed laser beam for detecting the ultrasound. Phase modulated light from the second laser beam is then demodulated to obtain a signal representative of the ultrasonic motion at the surface of the work piece. A disadvantage of such a system has been that in order to improve the systems ability to detect ultrasonic motion at the surface of the work piece a more powerful laser is required which suffers from the same problems as the '166 patent.

Another method to generate and detect ultrasound using lasers is disclosed in U.S. Pat. No. 5,137,361, issued Aug. 11, 1992, to Heon et. al. (the "361 patent"). The '361 patent discloses the use of a laser to detect deformations of a oscillatory or transient nature on a remote target surface. The deformations on the remote target surface can be produced by an ultrasound wave or other excitation. Light from the laser is scattered by the deformations, some of which light is collected by collecting optics and transmitted via a fiber optic to a beam splitter which deflects a small portion of the collected light to a reference detector and delivers the remaining portion of the light to a confocal Fabry-Perot interferometer, which generates an output signal indicative of the deformations on the remote target surface. The reference detector measures the intensity of the scattered laser light at the input of the interferometer to generate a reference signal. A stabilization detector measures the intensity of the scattered laser light at the output of the interferometer to generate a prestabilization signal. The ratio of the reference signal to the prestabilization signal is used to generate a final stabilization signal which drives a piezo-electric pusher inside the interferometer to adjust its resonant frequency. A disadvantage of such a system has been that a portion of the signal is lost at the beam splitter when sent to the reference detector. Again in order to improve the systems ability to detect ultrasonic motion at the surface of the work piece a more powerful laser is required.

An alternate to using a more powerful laser is to decrease the working distance to the part and/or increase the collection aperture size. This reduces the F-number of the optical system and has the disadvantage of a corresponding reduction in the working depth of field (DOF). DOF is a measure of how far away from the ideal focal plane an object can be and still maintain acceptable performance. Lower F-number designs generally result in smaller scan area capability and often require active focusing lens assemblies to maintain efficient light collection while scanning complex shaped components. Large collection apertures require the use of single-mirror optical scanning systems, usually in a two-axis gimbal configuration, that are cumbersome and generally slow.

Moreover, there is a need for a ultrasonic laser system which improves detection capabilities of the system to detect ultrasonic motion at the surface of the workpiece using practical lasers without damaging the workpiece and functioning with sufficiently large DOF.

SUMMARY OF THE INVENTION

The present invention provides a system and method for detecting ultrasonic surface displacements on a remote target that substantially eliminates or reduces disadvantages and problems associated with previously developed laser ultrasonic systems and methods.

More specifically, the present invention provides a system and method for detecting ultrasonic surface displacements on a target. The system for detecting ultrasonic surface displacements on a target includes a detection laser to generate a first pulsed laser beam to detect the ultrasonic surface displacements at the remote target. Collection optics collect the phase modulated light from the first pulsed laser beam scatered by the remote target. Scattering of the laser beam by the remote target includes all reactions between laser beam and the remote target where the laser beam is redirected with phase modulations induced by surface vibrations or perturbations such as those produced by ultrasonic mechanisms.

An optical amplifier amplifies the phase modulated light collected by the collection optics. This optical signal is in turn processed by an interferometer to process the phase modulated light and generate at least one output signal. Furthermore, a processor processes the at least one output signal to obtain data representative of the ultrasonic surface displacement on a remote target.

Another embodiment of the present invention includes a method for detecting ultrasonic surface displacements. This method includes the steps of first generating ultrasonic surface displacements at a remote target. These ultrasonic displacements at the remote target scatter the first pulsed laser beam creating a phase modulated return. This phase modulated light from the first pulsed laser beam either reflected or scattered by the remote target is then collected and optically amplified. This signal is processed to obtain data representative of the ultrasonic surface displacements at the remote target.

A technical advantage of the present invention is that an improved method for ultrasonic laser testing is provided. That provides rapid, non-contact, and non-destructive inspection techniques that can be applied to complex composite structures. The present invention provides a flexible, accurate and cost effective method for inspecting complex composite structures that is able to rapidly scan and test large-sized composite structures.

Another technical advantage of the present invention is an improved signal-to-noise ratio for the test system due to increased detection intensities reducing the required intensity of the detection laser.

Another technical advantage of the present invention is the ability to use a detection laser with lower output power.

Another technical advantage of the present invention is the possibility of an increased working distance between the target object and the scanner by optically amplifying the phase modulated light.

Yet another technical advantage is eliminating the need for active focusing elements due to the increased depth-of-field, which increases scan coverage, and is compatible with small-aperture high-speed optical scanners.

BRIEF DESCRIPTION OF THE DRAWINGS

For a more complete understanding of the present invention and advantages thereof, reference is now made to the following descriptions taken in conjunction with the accompanying drawings in which like reference numbers indicate like features and wherein.

DETAILED DESCRIPTION OF THE INVENTION

Figure 1:
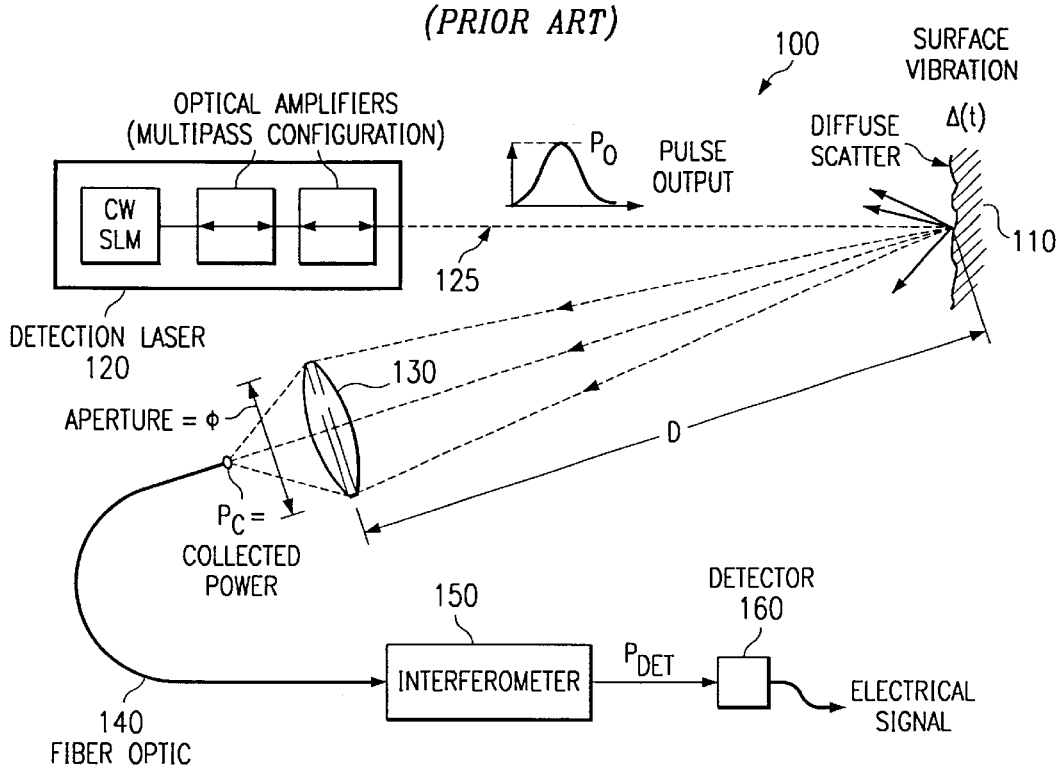
FIG. 1 illustrates a known setup for detecting ultrasonic surface displacements using a detection laser beam.

Preferred embodiments of the present invention and its advantages are understood by referring to FIGS. 1 through 7 of the drawing, like numerals being used for like and corresponding parts of the various drawings. The systems and methods of DRAKE are incorporated by reference in the present invention.

FIG. 1 illustrates a known setup for generating and detecting ultrasonic surface displacements using a detection laser beam. Detection system 100 utilizes a detection laser 120 to detect ultrasonic surface displacements on a remote target. Detection laser 120 may incorporate a continuous wave (cw) single longitudinal-mode (SLM) seed laser along with a multi-pass optical amplifier to generate a laser beam 125 with a power $P_o$. The ultrasonic surface displacements in the remote target 110 modulate, scatter and reflect detection laser beam 125, represented by arrows directed away from the remote target 110. When detection laser beam 125 interacts with the ultrasonic waves present in the remote target 110, detection laser beam 125 is reflected as phase-modulated light. Specifically considering the electric field representation of an incident laser beam 125 as:

$$E_{in} = E \cdot e^{i(\omega t - kx)}$$

where E is the electric field amplitude, $\omega$ is the radial frequency, t is time, the wave vector is defined as $$k = \frac{2\pi}{\lambda},$$

$\lambda$ is the wavelength, and x is the distance traveled to the target. Beam 125 is scattered or reflected from a surface 110 experiencing a time dependent displacement $\Delta(t)$, and returns along the same path, producing a modulated electric field for $\Delta(t) \ll \lambda$ defined as:

$$E_{in} = E \cdot [1 - 2ik\Delta(t)] e^{i\omega t}$$

The $\Delta(t)$ term must be demodulated using interferometer 150 from this expression for reconstruction of the time history of the surface displacement. Some of the phase modulated light is captured by collection optics 130, which directs the phase-modulated light via fiber optic 140 into interferometer 150. Interferometer 150 demodulates the phase-modulated light and directs its outputs into detector 160 which generates an analog signal for processing.

Collection optics 130 has an aperture diameter of $\phi$ and is spaced a distance D from remote target 110. The power of the collected, phase-modulated light as measured at the output of the collector is $P_c$, and therefore, the power at the input of the interferometer is substantially $P_c$ since there is very little transmission loss associated with fiber optic 140. A typical diffuse surface will have the following relationship describing the amount of collected light for a specified optic diameter and working distance:

$$P_c = \frac{P_o}{4}\left(\frac{\Phi}{D}\right)^2 (1-A)\cos(\theta)$$

Where A represents the absorption of the target and θ is the angle of incidence. A perfect white diffuse target would have A=0, and a typical dark composite might have an absorption of 90% (A=0.9). Because the loss in interferometer 150 is minimal, the power of the input signal to the detector ($P_{DET}$) is substantially the same as $P_c$.

The signal-to-noise ratio for shot-noise limited performance of detector 160 is directly proportional to the square root of the input power:

$$SNR = \sqrt{\frac{R_\lambda P_{det}}{2eBW}}$$

where $R_\lambda$ is the responsivity of the detector, e the electron charge, and BW is the electrical bandwidth. It is assumed that the electrical bandwidth of detector 160 is restricted to be the smallest possible for the measurement of interest and that detector 160 is near optimal for the intended wavelength.

The formula above suggests that the SNR can be improved by increasing $P_o$, or ϕ, or by decreasing D. Increasing the ratio of ϕ/D (lowering the F-number) will decrease the depth of field of detection system 100, which is undesirable because a decreased depth of field is less flexible and may necessitate the use of active focusing optics.

Figure 2:
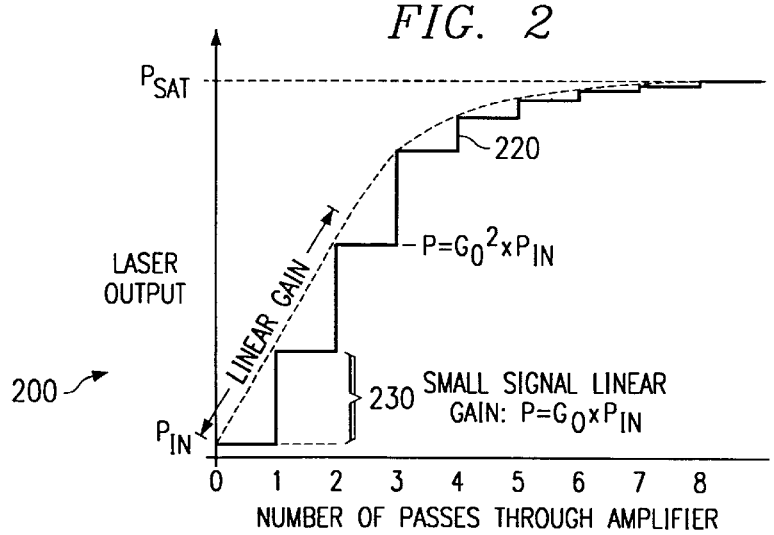
FIG. 2 is a typical gain plot for an optical amplifier illustrating laser output versus number of passes through the amplifier.

Alternatively, $P_o$ can be increased. One approach to increase the output of detection laser 120 is to use a shorter pulse width while maintaining the same pulse energy thereby increasing the peak power. The pulse of detection laser beam 125, however, must be of a sufficient duration to permit detection of ultrasonic surface displacements for materials with various thickness, and therefore, decreasing its pulse duration degrades its ability to detect such displacements on a variety of materials. A second approach is to amplify the detection laser using a multiple pass optical amplifier. However, the gain of a conventional optical amplifier is dependent upon the power of the input signal. FIG. 2 illustrates a gain plot 200 for a typical optical amplifier as a function of the number of passes through the amplifier. Gain plot 200 shows that the typical amplifier has a linear gain 210 for small input signals. However, the gain 220 is not linear as the input signal increases, as illustrated by the leveling of gain plot 200 as the amplifier approaches saturation. Gain plot 200 demonstrates that adding multiple amplifier passes quickly reaches a point of diminishing returns, and therefore, the ability to increase SNR by increasing $P_o$, is limited. Adding more amplifier sections to further increase output power is very costly. Cost will increase in direct proportion to the power addition, to double power will double cost.

Figure 3:
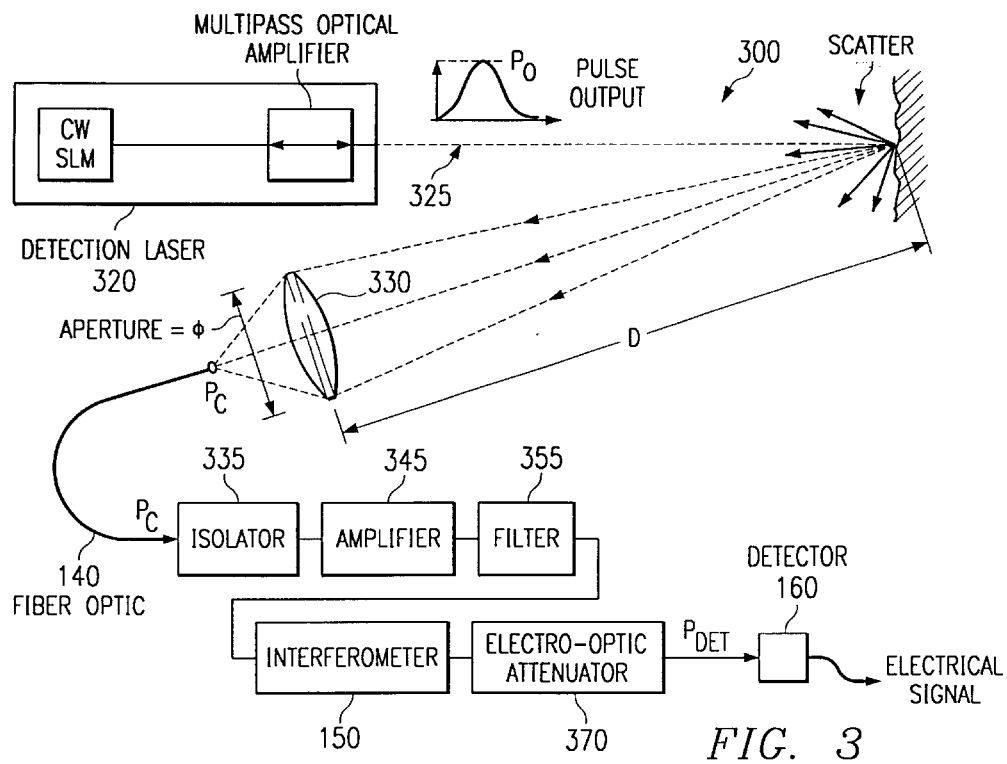
FIG. 3 illustrates the use of a post-collection multipass optical amplifier to yield an improved signal-to-noise ratio.

FIG. 3 illustrates a setup for a new and improved detection system 300. Detection system 300 utilizes a detection laser 320 to detect ultrasonic surface displacements in a remote target 110. Detection laser 320 may incorporate a multi-pass optical amplifier to generate a laser beam 325 with a power $P_o$.

The ultrasonic surface displacements, Δ(t), in a remote target 110 may be produced using a generation laser, a piezoelectric transducer, electrical discharge, projectile impact or other known means. The ultrasonic surface displacements modulate, scatter and reflect detection laser beam 325. When detection laser beam 325 interacts with the ultrasonic waves present at the remote target 110, detection laser beam 325 is reflected as phase-modulated light, as illustrated by the arrows directed away from remote target 110.

When a generation laser is used to induce ultrasonic surface displacements, the generation laser must be of a frequency that is readily absorbed into the remote target 110 without causing ablation or breaking down the remote target material, and it must be of sufficient pulse length to induce ultrasonic surface deformations. For example, a transverse-excited atmospheric ("TEA") $CO_2$ laser can be used to produce a 10.6 micron wavelength beam for a 100 nanosecond pulse. The power of the laser must be sufficient to deliver, for example, a 0.25 joule pulse to the remote target, which may require a 100 watt laser operating at 400 Hz pulse rate. The generation laser should be absorbed as heat into the remote target thereby causing thermoelastic expansion without ablation. Optionally, the generation laser and the detection laser may also be applied coaxially to the surface of the remote target object.

The detection laser 320 must be of a sufficiently long pulse duration that it does not induce ultrasonic surface displacements. For example, a long-pulsed Nd:YAG laser can be used. The power of this laser must be sufficient to deliver, for example, a 20 milli-joule, 100 microsecond pulse, which may require 200 watt peak power laser.

When detection laser beam 325 interacts with the ultrasonic waves present in remote target 110, detection laser beam 325 is reflected as phase-modulated light. Some of the phase modulated light is captured by collection optics 330. Collection optics 330 may utilize either a large aperture collector or a small aperture collector. For example, a large aperture collector may be a Cassegrain-type reflector, comprised of a primary reflective surface which directs light upon a secondary reflective surface, which in turn, focuses the light into fiber optic 140. For increased speed and flexibility, however, a small aperture collector is desirable typically of a refractive doublet construction. The optical invariant or etendue should be appropriately matched between the collection optic 330 design and the collection fiber optic 140.

Collection optics 330 collect the phase-modulated light and directs it into fiber optic carrier 140, which in turn, directs the phase-modulated light through optical isolator assembly 335 into optical amplifier 345. Isolator assembly 335 is employed to minimize the possibility of self-oscillation of the amplifier 345 due to Fresnel reflections form the collection fiber 140 end face. The amplified, phase-modulated light is directed through an optical filter 355. Optical filter 355 is employed, as necessary, to reduce noise generated in amplifier 345. The amplified and filtered, phase-modulated light is then directed into interferometer 150, wherein the light is demodulated. The demodulated light is then directed into an electro-optic attenuator 370, to manage the light intensity, and finally into detector 160 which generates an analog output signal.

Optionally, an optical ranging unit (not shown) can be integrated into detection system 300 to utilize a ranging laser beam to determine the distance between the remote target 110 and the scanning system. Often, it is important to know the distance by which remote target 110 is located from the scanner so that a topographical contour can be created for the remote target and can be correlated to the optical data being collected. Generally, this correlation is recorded on a point-by-point basis.

The power of the collected, phase-modulated light as measured at the output of the collector is $P_c$, and optical amplifier 345 has a gain G. Therefore, the power of the signal at the output of optical amplifier is $P_c*G$.

The post-collection amplification process must be analyzed for linearity, bandwidth and noise performance to determine suitability for a particular application. As noted in FIG. 2, these amplifiers will be suitable for linear, undistorted, amplification of small input signals, and the known saturation effects could be removed by post-processing if operated at higher input levels. In regard to bandwidth, as an example, Nd:YAG has a spontaneous-emission spectrum width on the order of 150 GHz. Gain bandwidth narrowing of the 150 GHz Lorentzian line-shape can reduce the bandwidth down to values as low as 30 GHz for very high gain amplification. The effective optical bandwidth dv can be deinied as:

$$dv = dv_o \frac{1}{F} \sqrt{\frac{3}{G-3}}$$

where $dv_o$ is the spontaneous-emission line width, F is the filter 355 finesse, and G is the amplifier 345 gain in dB.

Thus, even at high gains, this method will function for ultrasonic frequencies of interest, which usually are below 100 MHz. As an example, composite material testing only requires a 10 MHz bandwidth.

Noise contribution from the optical amplifier can be described using the Noise Equivalent Power (NEP) approach where the amplifier output noise is referenced back to an equivalent amount of signal that would produce the observed noise level. The source of the amplifier noise is due to amplified spontaneous emissions (ASE), which are fundamental to all optical amplifiers. Four-level amplification systems are superior to three-level systems in this application due to the transitions occurring down to relatively unpopulated levels thereby a minimum number of ASE producing inverted states are necessary for a particular gain requirement. The NEP for an optical amplifier 345 that is etendue matched to a collection fiber optic 140 is given as:

$$NEP = 2hv(dv)\left(\frac{\pi a_o NAn}{\lambda}\right)^2$$

Where h is Planks constant, v is the optical frequency, dv is the optical bandwidth (includding gain narrowing and filtering processes), $\alpha_o$ is the half-diameter of the collection fiber optic 140, NA is the numerical aperture of 140, n is the index of refraction of the gain medium 345, and $\lambda$ is the optical wavelength. It is possible to reduce the NEP by optical filtering with 355 to lower the gain-narrowed bandwidth from 30 GHz down to 1 GHz using a simple plane fabry-perot device with a finesse of 30. Further reduction is possible if necessary, potentially matching the desired electrical bandwidth BW.

Two primary noise terms must be considered at the electrical detector. First, both the signal and the ASE will generated shot-noise in the detector, although by employing optical filter 355 it is possible to reduce the ASE sufficiently below Pc such that all shot-noise contributions are dominated by that produced by the signal component alone. A design goal might be to maintain the ASE at least one-third of the signal level for the weakest predicted value of Pc.

The second noise contribution occurs from hetrodyne mixing of the ASE with the signal within the electrical bandwidth of the detector. This noise is not reduced by optical filtering, although it is common-mode and can be reduce through the use of a differential interferometr 150, where the hetrodyne noise can be subtracted from a pair of balanced detectors.

Noise performance is often limited by the relative intensity noise (RIN) of the continuous-wave (cw) single-longitudinal mode (SLM) laser that is part of detection laser 320. This noise term is also common-mode and can be reduced by using a differential interferometer 150.

Neglecting common-mode noise terms due to RIN and hetrodyne mixing, the signal-to-noise ratio of detector 160 is directly proportional to the square root of the input power and increases with amplifier gain G in the limiting case where the NEP<<Pc:

$$SNR = \sqrt{\frac{GR_\lambda P_c^2}{2e(P_c + NEP)}}$$

The introduction of the optical amplifier to amplify $P_c$, however, permits the SNR to be improved by increasing $P_{det}$, in addition to increasing $P_o$, or $\Phi$, or by decreasing D. There are several added advantages, however. It is no longer critical to increase $P_o$ to the maximum, and therefore, any amplifier that amplifies detection laser 320 such that Pc>>NEP can be employed. For some system configurations, it is possible for a cw SLM laser to provide sufficient performance that laser 320 could operate without an amplifier section. Moreover, optical amplifier 345 can also be operated in the efficient, linear gain region where gains of 100 dB are possible. The increased performance associated with a two amplifier approach (one amplifier in detection laser 120, and one amplifier post-collection), will permit the system to use a smaller aperture and a greater distance D, therefore, providing detection system 300 with greater flexibility without any degradation in performance. On the contrary, detection system 300 enjoys increased performance.

Moreover, optical amplifier 345 will not contribute any substantial additional noise unless $P_c$<<NEP. Thus, the post-collection optical amplification approach improves the SNR without any substantial increase in noise. Electrical amplification of the analog signal subsequent to detector 160, however, will not improve the SNR above $P_c$. This is so because both the signal and the noise component will be amplified. The following example illustrates embodiments of the present invention, but should not be viewed as limiting the scope of the invention.

Consider a laser 320 that produces a peak output power of 100 W, a collection optic 330 that is 45 mm in diameter operating at a distance D of 3000 mm from the target which has an absorption of 90%. The collected light Pc is coupled with a 50% efficiency to a 200 um fiber optic 140 with a NA=0.22. In this example, the collection fiber optic 140 is slightly underfilled, but provides a large DOF. Using a filter 355 finesse of 30 for a Nd:YAG amplifer 345 with index 1.8 and wavelength of 1064 nm we arrive at a NEP=5 uW and a Pc=280 uW. After polarization effects are factored, both the NEP and Pc will typically be half but the ratios remain unchanged. Assuming an amplifier gain G=100,000 with a 20% efficiency after passing through the filter 355 and other optical components there will be approximately 2.8 W of signal power to be processed by interferometer 150 and possibly reduced in intensity by attenuator 370 prior to reaching signal detectors 160. In this example, the noise performance would be dominated by residual RIN from the cw SLM laser, yet can function at very large distances with a small collection aperture.

Figure 4:
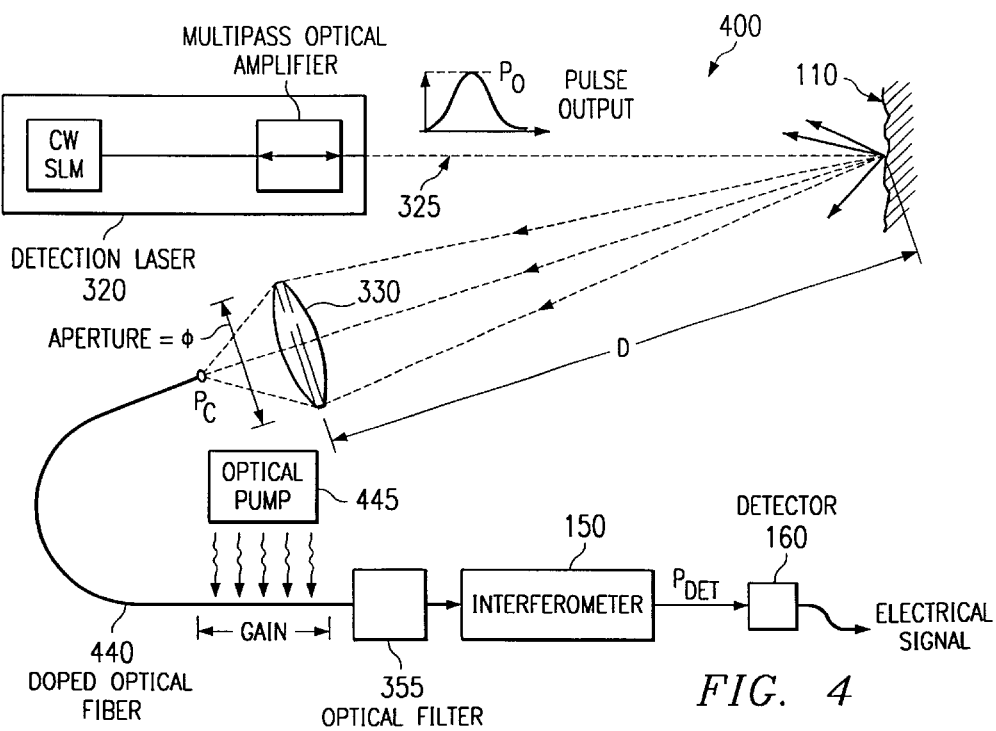
FIG. 4 illustrates the use of doped fiber optic and an optical pump for post-collection optical amplification.

FIG. 4 illustrates a second embodiment to achieve post-collection optical amplification. The setup illustrated in FIG. 4 is very similar to that presented in FIG. 3, and therefore, only the differences will be discussed here. Collection optics 330 collect the phase-modulated light and direct it into a doped fiber optic carrier 440, which in turn, directs the phase-modulated light into interferometer 150, wherein the light is demodulated. The demodulated light is then directed into detector 160 which generates an analog output signal. An optical pump 445 is coupled to doped fiber optic carrier 440, and acts as an amplifier to increase the power of the signal. The amplified, phase-modulated light is directed through optical filter assembly 355 prior to being delivered to interferometer 150. The combination of doped fiber optical carrier 440 and optical pump 445 results in an effective gain of $e^{2aL}$. Of course, a specific optical amplifier is not critical to the present invention, and therefore, other known optical amplifiers may be used.

Figure 5:
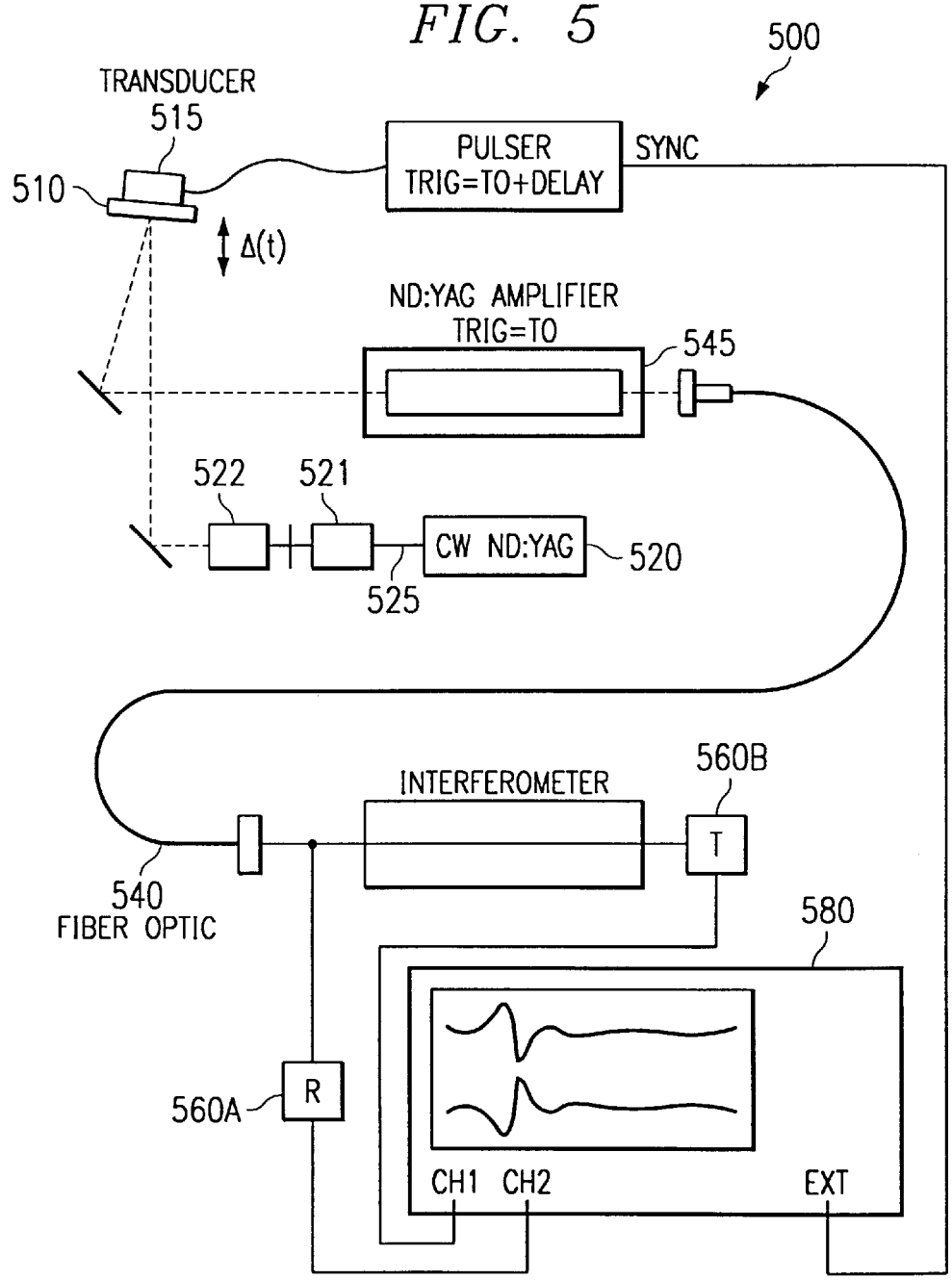
FIG. 5 illustrates a setup for testing the gain associated with post-collection optical amplification.

FIG. 5 illustrates a setup for testing the use of post-collection optical gain approach of the present invention. Detection laser 520 generates a detection laser beam 525 which is directed upon a remote target 510 to detect ultrasonic surface displacements thereon. Detection laser beam 525 is amplified by two external amplifiers 521, 522 before being directed upon surface 510.

In this test setup, the ultrasonic surface displacements in remote target 510 are produced using a piezoelectric transducer 515, which transducer is synchronized using synchronizing means 570. The ultrasonic surface displacements modulate, scatter and reflect detection laser beam 525. When detection laser beam 525 interacts with the ultrasonic waves present in remote target 510, detection laser beam 525 is reflected as phase-modulated light from remote target 510. The reflected, phase-modulated light is collected and directed into optical amplifier 545 where it may be amplified if desired, or may be passed through without amplification, depending on whether amplifier 545 is active or inactive. From amplifier 545, the light is directed via fiber optic 140 into interferometer 150, wherein the reflected and transmitted components of the signal are detected using detectors 560A and 560B, respectively. Detectors 560A and 560B generate analog signals which are then captured for comparison by measurement device 580.

Figure 6:
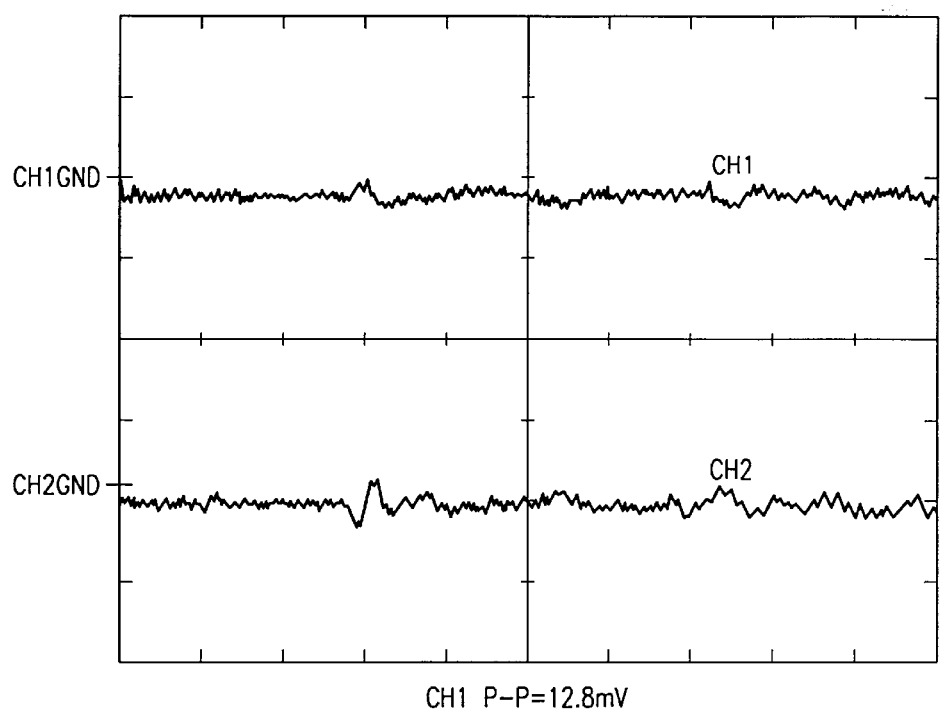
FIG. 6 illustrates reflected and transmitted signals generated using the setup of FIG. 5 without post-collection optical amplification.

FIG. 6 illustrates the reflected and transmitted signals as detected when amplifier 545 is inactive, and thus, passes the collected, phase-modulated light without amplification.

Figure 7:
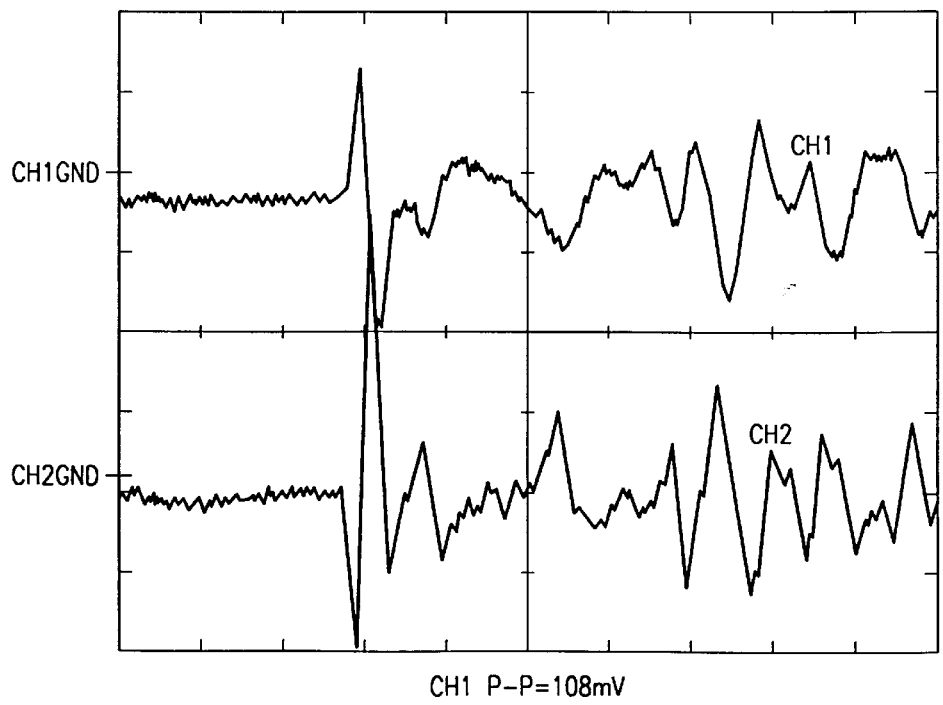
FIG. 7 illustrates reflected and transmitted signals generated using the setup of FIG. 5 with post-collection optical amplification.

FIG. 7 illustrates the reflected and transmitted signals as detected when amplifier 545 is active, and thus, amplifies the collected, phase-modulated light. A comparison of the signals illustrated in FIGS. 6 and 7 demonstrates that the reflected and transmitted signals have been amplified significantly without any substantial increase in noise.

Although the present invention has been particularly shown and described in detail, it should be understood that various changes, substitutions and alterations can be made hereto without departing from the spirit and scope of the invention as defined in the appended claims.

What is claimed is:

1. A method for detecting ultrasonic surface displacements on a target, comprising the steps of:

generating ultrasonic surface displacements at the target;

using a first pulsed laser beam to detect the ultrasonic surface displacements at the target;

collecting phase modulated light from the first pulsed laser beam scattered by the target;

optically amplifying collected phase modulated light; and processing the collected phase modulated light to obtain data representative of the ultrasonic surface displacements at the target.

2. The method of claim 1, further comprising preventing reflected phase modulated light feedback into an optical amplifier with at least one optical isolation assembly placed in the path of propagation of the phase modulated light which has been collected.

3. The method of claim 1, wherein the step of processing the phase modulated light further comprises the steps of:

Using an interferometer to demodulate the phase modulated light for creating at least one optical signal;

converting the at least one optical signal into at least one digital signal; and using a digital signal processor to process the at least one digital signal.

4. The method of claim 2, wherein the step of converting the at least one optical signal into at least one digital signal further comprises the steps of:

converting the at least one optical signal into at least one analog signal; and converting the at least one analog signal into at least one digital signal.

5. The method of claim 1, wherein the ultrasonic surface displacements at the target are generated using a second pulsed laser beam and wherein the first pulsed laser beam is applied coaxially with the second pulsed laser beam.

6. The method of claim 1, wherein the step of optically amplifying the phase modulated light is accomplished using a multi-pass optical amplifier.

7. The method of claim 1, wherein the step of optically amplifying the phase modulated light is accomplished using a doped fiber optic carrier coupled to an optical pump.

8. The method of claim 1, further comprising amplifying the first pulsed laser beam prior to applying it to the target.

* * * * *